(12) United States Patent
Hanada et al.

(10) Patent No.: US 8,975,420 B2
(45) Date of Patent: *Mar. 10, 2015

(54) FIVE-MEMBERED CYCLOCARBONATE POLYSILOXANE COMPOUND AND PROCESS FOR PREPARATION OF SAME

(75) Inventors: Kazuyuki Hanada, Tokyo (JP); Kazuya Kimura, Tokyo (JP); Kenichi Takahashi, Tokyo (JP); Osamu Kawakami, Tokyo (JP); Manabu Uruno, Tokyo (JP)

(73) Assignees: Dainichiseika Color & Chemicals Mfg. Co., Ltd., Tokyo (JP); Ukima Chemicals & Color Mfg. Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/503,936

(22) PCT Filed: Oct. 7, 2010

(86) PCT No.: PCT/JP2010/067679
§ 371 (c)(1),
(2), (4) Date: Apr. 25, 2012

(87) PCT Pub. No.: WO2011/065129
PCT Pub. Date: Jun. 3, 2011

(65) Prior Publication Data
US 2012/0232289 A1 Sep. 13, 2012

(30) Foreign Application Priority Data

Nov. 25, 2009 (JP) ................................ 2009-267052
Mar. 31, 2010 (JP) ................................ 2010-081907

(51) Int. Cl.
*C07D 307/04* (2006.01)
*C07D 307/77* (2006.01)

(52) U.S. Cl.
USPC ........................................ 549/214; 549/200

(58) Field of Classification Search
USPC ................................................ 549/200, 214
See application file for complete search history.

(56) References Cited

U.S. PATENT DOCUMENTS

| 3,072,613 | A | 1/1963 | Whelan et al. |
| 4,480,009 | A | 10/1984 | Berger |
| 4,499,149 | A | 2/1985 | Berger |
| 4,883,854 | A | 11/1989 | Coury et al. |
| 4,895,829 | A | 1/1990 | Hanada et al. |
| 4,910,087 | A | 3/1990 | Torii et al. |
| 5,606,077 | A | 2/1997 | Lersch et al. |
| 5,686,547 | A | 11/1997 | Nye |
| 6,120,905 | A | 9/2000 | Figovsky |
| 6,379,751 | B1 | 4/2002 | Shäfer et al. |
| 6,784,300 | B2 * | 8/2004 | Cetin et al. ................. 549/214 |

| 2006/0276599 | A1 | 12/2006 | DeWitt et al. |
| 2007/0059597 | A1 | 3/2007 | Nakanishi et al. |
| 2007/0134502 | A1 | 6/2007 | Fonda |
| 2007/0135588 | A1 | 6/2007 | Diakoumakos et al. |
| 2009/0018302 | A1 | 1/2009 | Laas et al. |
| 2010/0210809 | A1 | 8/2010 | Simon et al. |
| 2011/0039948 | A1 | 2/2011 | Lange et al. |
| 2012/0231184 | A1 | 9/2012 | Hanada et al. |

(Continued)

FOREIGN PATENT DOCUMENTS

| EP | 390777 | 10/1990 |
| EP | 1143063 | 10/2001 |

(Continued)

OTHER PUBLICATIONS

Lang et al (2009): STN International HCAPLUS database, Columbus (OH), accession No. 2009: 1141958.*

(Continued)

*Primary Examiner* — Golam M Shameem
(74) *Attorney, Agent, or Firm* — Hamre, Schumann, Mueller & Larson, P.C.

(57) ABSTRACT

A 5-membered cyclic carbonate polysiloxane compound is represented by the below-described formula (1), and is produced by a process that reacts an epoxy-modified polysiloxane compound with carbon dioxide.

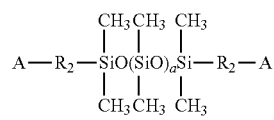

(1)

wherein A means

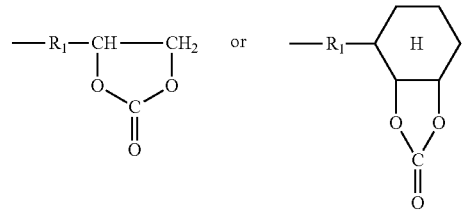

in which $R_1$ means an alkylene group which has from 1 to 12 carbon atoms and may be linked via an element of O, S or N and/or —$(C_2H_4O)_b$—, $R_2$ means a direct bond or an alkylene group having from 2 to 20 carbon atoms, $R_2$ may be linked to an alicyclic group or aromatic group, b stands for a number of from 1 to 300, and a stands for a number of from 1 to 300.

8 Claims, 2 Drawing Sheets

(56) References Cited

U.S. PATENT DOCUMENTS

| | | |
|---|---|---|
| 2012/0237701 A1 | 9/2012 | Hanada et al. |
| 2013/0171896 A1 | 7/2013 | Hanada et al. |
| 2014/0024274 A1 | 1/2014 | Hanada et al. |

FOREIGN PATENT DOCUMENTS

| | | |
|---|---|---|
| EP | 2505600 | 10/2012 |
| EP | 2010276 | 7/2013 |
| JP | 56-4408 | 1/1981 |
| JP | 58-13359 B | 3/1983 |
| JP | 61-227087 | 10/1986 |
| JP | 62-202786 | 9/1987 |
| JP | 2-102096 | 4/1990 |
| JP | 3-501121 | 3/1991 |
| JP | 06-025604 | 2/1994 |
| JP | 06-247151 | 9/1994 |
| JP | 8-109349 | 4/1996 |
| JP | 8-225670 | 9/1996 |
| JP | 8-245791 | 9/1996 |
| JP | 9-278982 | 10/1997 |
| JP | 10-67857 | 3/1998 |
| JP | 10-251405 | 9/1998 |
| JP | 11-140182 | 5/1999 |
| JP | 2000-319504 | 11/2000 |
| JP | 2001-234071 | 8/2001 |
| JP | 2002-114936 | 4/2002 |
| JP | 2002-518532 | 6/2002 |
| JP | 2004-51901 | 2/2004 |
| JP | 2005-154580 | 6/2005 |
| JP | 2005-336637 | 12/2005 |
| JP | 2006-176615 | 7/2006 |
| JP | 2006-307015 | 11/2006 |
| JP | 2006-336015 | 12/2006 |
| JP | 2007-501886 | 2/2007 |
| JP | 2007-77075 | 3/2007 |
| JP | 2007-270373 | 10/2007 |
| JP | 2007-297544 | 11/2007 |
| JP | 2008-56772 | 3/2008 |
| JP | 2008-297552 | 12/2008 |
| JP | 2009-30050 | 2/2009 |
| JP | 2009-520082 | 5/2009 |
| JP | 2009-144313 | 7/2009 |
| JP | 2009-155407 | 7/2009 |
| JP | 2011-132509 | 7/2011 |
| KR | 1986-0002192 B | 12/1986 |
| WO | WO 89/00565 | 1/1989 |
| WO | WO 2008/142109 | 11/2008 |
| WO | WO 2009/112418 | 9/2009 |
| WO | WO 2011/065129 | 6/2011 |
| WO | WO 2011/065432 | 6/2011 |
| WO | WO 2011/065433 | 6/2011 |
| WO | WO 2011/162237 | 12/2011 |
| WO | WO 2012/026338 | 3/2012 |

OTHER PUBLICATIONS

N. Kihara et al.: "Catalytic Activity of Various Salts in the Reaction of 2,3-Epoxypropyl Phenyl Ether and Carbon Dioxide under Atmospheric Pressure"; J. Org. Chem. 58, 6198-6202 (1993)—5 pages.

N. Kiraha et al.: "Synthesis and Properties of Poly (hydroxyurethane)s"; Journal of Polymer Science, Part A: Polymer Chem., 31(11), 2765-2773 (1993)—9 pages.

Zhu et al.: "New polysiloxanes bearing cyclic carbonate side chains: synthesis and ionic conductivity studies"; Polymer Preprints (1994) vol. 35, No. 1, p. 496-497—2 pages.

Zhu et al.: "Synthesis of Polysiloxanes Bearing Cyclic Carbonate Side Chains. Dielectric Properties and Ionic Conductivities of Lithium Triflate Complexes"; Macromolecules (1994) vol. 27, No. 15, p. 4076-4079—4 pages.

* cited by examiner

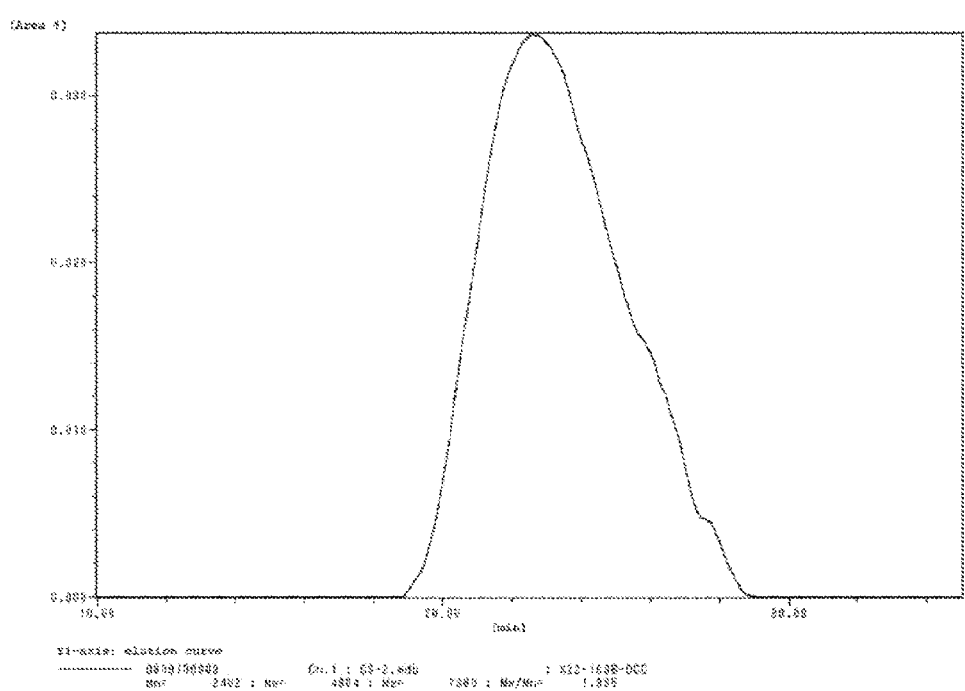

FIVE-MEMBERED CYCLOCARBONATE POLYSILOXANE COMPOUND AND PROCESS FOR PREPARATION OF SAME

TECHNICAL FIELD

This invention relates to a novel 5-membered cyclic carbonate polysiloxane compound and its production process. More specifically, the present invention is concerned with a novel 5-membered cyclic carbonate polysiloxane compound, which is excellent in lubricity, abrasion resistance, chemical resistance, non-tackiness, antistatic properties and heat resistance, is also superb in carbon dioxide reduction effect from the viewpoint of the global environment, and is useful as a raw material for film and mold forming materials, sealants, various coating materials and various binders, and also with a process for producing the 5-membered cyclic carbonate polysiloxane compound.

BACKGROUND ART

Five-membered cyclic carbonate compounds, which make use of carbon dioxide as a raw material, are known for some time as reported in Non-patent Documents 1 and 2. Under the current situation, however, the development of their applications has not moved ahead, because high-molecular compounds synthesized from the above-described, conventionally-known compounds as starting materials are evidently inferior in characteristics to fossil-based, high-molecular compounds (see Patent Documents 1 and 2).

However, the global warming phenomenon which can be considered to be attributable to the ever-increasing emission of carbon dioxide in recent years has become a worldwide problem, and a reduction in carbon dioxide emissions has arisen as a critical issue for the entire world. The change to renewable resources such as biomass and methane has also become a worldwide trend from the viewpoint of the problem of exhaustible fossil resources (petroleum).

Under such a background as described above, 5-membered cyclic carbonate compounds are drawing a fresh look again. Carbon dioxide, which is a raw material for these compounds, is a readily-available and sustainable carbon resource, and moreover, plastics that make use of carbon dioxide as a replacement for fossil resources can be considered to be effective means for resolving problems such as global warming and resource depletion.

PRIOR ART DOCUMENTS

Patent Documents

Patent Document 1: U.S. Pat. No. 3,072,613
Patent Document 2: JP-A-2000-319504

Non-Patent Documents

Non-patent Document 1: N. Kihara, N. Hara, T. Endo, J. Org. Chem., 58, 6198 (1993)
Non-patent Document 2: N. Kihara, T. Endo, J. Polymer Sci., Part A Polymer Chem., 31(11), 2765 (1993)

DISCLOSURE OF THE INVENTION

Problem to be Solved by the Invention

To use, for example, polyhydroxy polyurethane resins, which are obtainable by using 5-membered cyclic carbonate compounds that make use of carbon dioxide as a raw material, for industrial applications in much the same way as conventional fossil-based high-molecular compounds (plastics), the polyhydroxy polyurethane resins, however, need to be provided with improved performance and a new additional value. Described specifically, from the viewpoint of making further contributions to the protection of the global environment, there is an outstanding desire in the above-described case to develop compounds which make use of carbon dioxide as a raw material and enable to obtain polyhydroxy polyurethane resins improved in performance indispensable for industrial applications, such as still higher heat resistance, chemical resistance, abrasion resistance, and so on. An object of the present invention is, therefore, to provide a technology that can realize such a desire.

Means for Solving the Problem

The above-described object can be achieved by the present invention to be described hereinafter. Specifically, the present invention provides a 5-membered cyclic carbonate polysiloxane compound represented by the following formula (1):

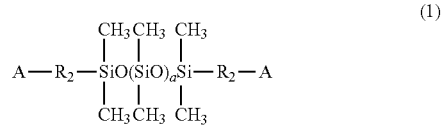

(1)

wherein A means

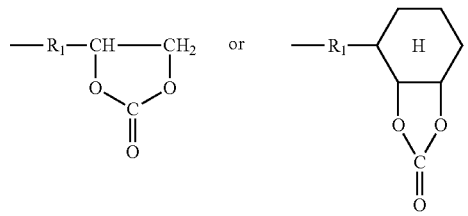

in which $R_1$ means an alkylene group which has from 1 to 12 carbon atoms and may be linked via an element of O, S or N and/or $-(C_2H_4O)_b-$, $R_2$ means a direct bond or an alkylene group having from 2 to 20 carbon atoms, $R_2$ may be linked to an alicyclic group or aromatic group, b stands for a number of from 1 to 300, and a stands for a number of from 1 to 300.

The present invention also provides a process for producing the above-described 5-membered cyclic carbonate polysiloxane compound, which comprises reacting an epoxy-modified polysiloxane compound represented by the following formula (2) with carbon dioxide:

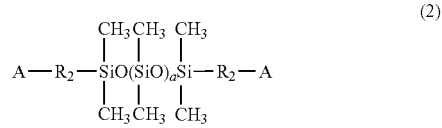

(2)

wherein A means

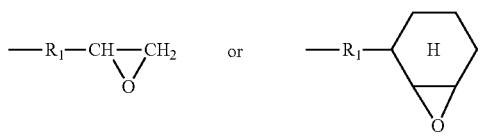

in which $R_1$ means an alkylene group which has from 1 to 12 carbon atoms and may be linked via an element of O, S or N and/or —$(C_2H_4O)_b$—, $R_2$ means a direct bond or an alkylene group having from 2 to 20 carbon atoms, $R_2$ may be linked to an alicyclic group or aromatic group, b stands for a number of from 1 to 300, and a stands for a number of from 1 to 300.

Advantageous Effects of the Invention

A polysiloxane-modified polyhydroxy polyurethane resin obtainable from the 5-membered cyclic carbonate polysiloxane compound according to the present invention is excellent in lubricity, abrasion resistance, chemical resistance, non-tackiness, antistatic properties, heat resistance and the like. Moreover, the use of the 5-membered cyclic carbonate polysiloxane compound according to the present invention makes it possible to provide a variety of environment-responsive products which can contribute to a reduction in greenhouse gas through the incorporation of carbon dioxide and is suited from the viewpoint of the protection of the global environment.

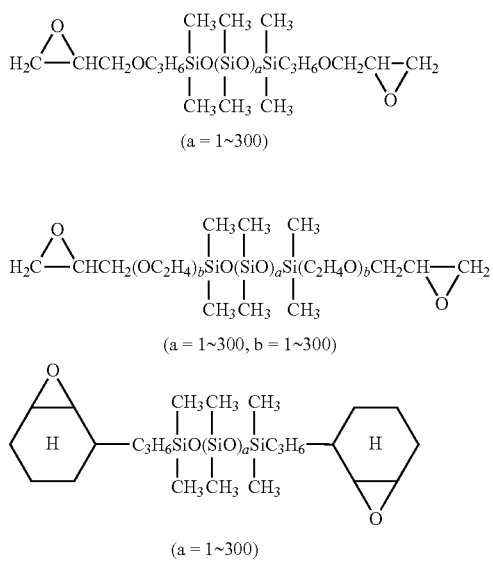

Figure 1:
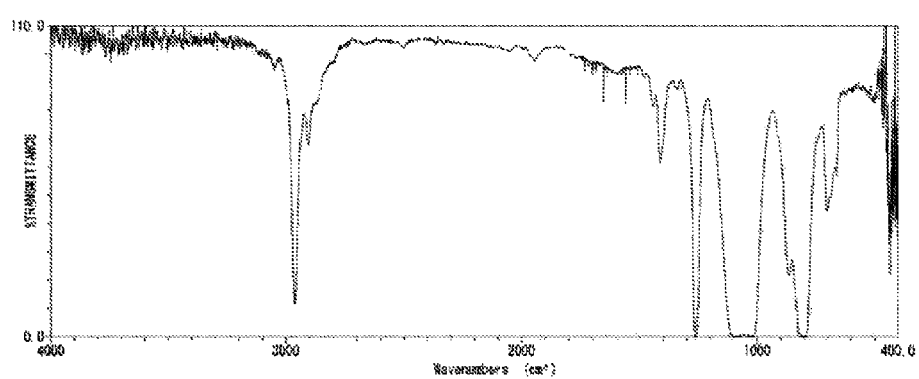
FIG. 1 is an infrared absorption spectrum of an epoxy-modified polysiloxane.

FIG. 3 shows a GPC elution curve of the 5-membered cyclic carbonate polysiloxane (mobile phase: THF, column: "TSK-GEL GMHXL+G2000HXL+G3000HXL", detector: IR detector)

MODES FOR CARRYING OUT THE INVENTION

The present invention will next be described in further detail based on preferred embodiments.

The 5-membered cyclic carbonate polysiloxane compound of the present invention represented by the formula (1) can be produced, for example, by reacting an epoxy-modified polysiloxane compound represented by the formula (2) with carbon dioxide as shown by the below-described "Equation-A". Described more specifically, it can be obtained by reacting the epoxy-modified polysiloxane compound with carbon dioxide in the presence or absence of an organic solvent, in the presence of a catalyst, at a temperature of from 40° C. to 150° C., under normal pressure or slightly elevated pressure, for from 10 to 20 hours.

Equation-A

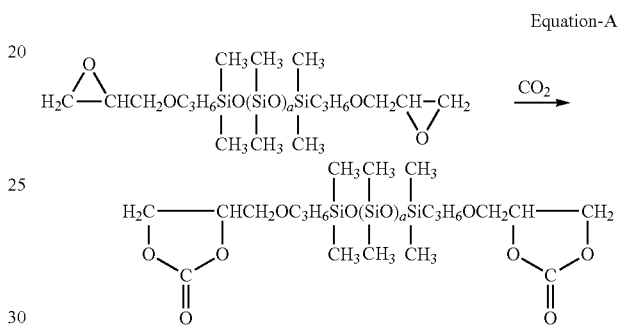

Usable examples of the epoxy-modified polysiloxane compound, which is represented by the formula (2) and is useful in the present invention, include such specific compounds as will be described below.

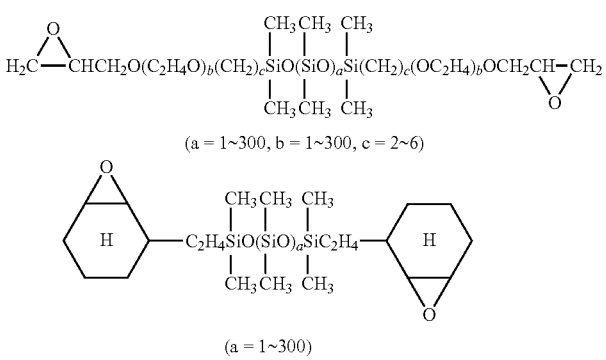

The above-listed epoxy-modified polysiloxane compounds are preferred compounds for use in the present invention, and the present invention shall not be limited to these exemplified compounds. Not only above-exemplified compounds but also other similar epoxy-modified polysiloxane compounds are available on the market these days. Accordingly, those readily available on the market can all be used in the present invention.

by the below-described "Equation-B". The reaction between the 5-membered cyclic carbonate polysiloxane compound and the polyamine can be conducted in the presence of an organic solvent at a temperature of from 20° C. to 150° C.

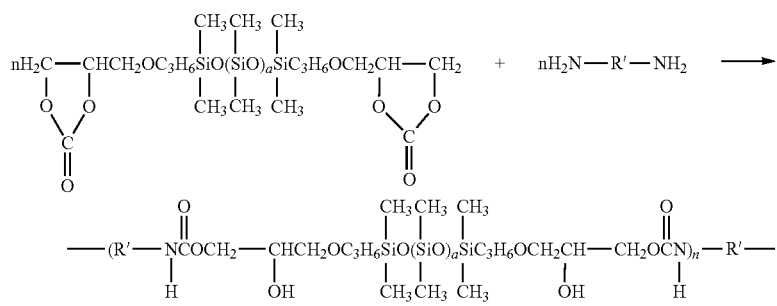

Equation-B

As described above, the 5-membered cyclic carbonate polysiloxane compound according to the present invention can be obtained through the reaction between the specific epoxy-modified polysiloxane compound and carbon dioxide. As catalysts usable in this reaction, base catalysts and Lewis acid catalysts can be mentioned.

The base catalysts include tertiary amines such as triethylamine and tributylamine; cyclic amines such as diazabicycloundecene, diazabicyclooctane and pyridine; alkali metal salts such as lithium chloride, lithium bromide, lithium fluoride and sodium chloride; alkaline earth metal salts such as calcium chloride; quaternary ammonium salts such as tetrabutyl ammonium chloride, tetraethyl ammonium bromide and benzyl trimethyl ammonium chloride; carbonate salts such as potassium carbonate and sodium carbonate; metal acetates such as zinc acetate, lead acetate, copper acetate and iron acetate; metal oxides such as calcium oxide, magnesium oxide and zinc oxide; phosphonium salts such as tetrabutyl phosphonium chloride; and the like.

The Lewis acid catalysts include tin compounds such as tetrabutyltin, dibutyltin dilaurate, dibutyltin diacetate and dibutyltin octoate.

The amount of the above-described catalyst maybe from 0.1 to 100 parts by mass, preferably from 0.3 to 20 parts by mass per 50 parts by mass of the epoxy-modified polysiloxane compound. If the above-described catalyst is used in an amount of smaller than 0.1 parts by mass, the catalyst will be unable to fully exhibit its effects as a catalyst. If the above-described catalyst is used in an amount of greater than 100 parts by weight, on the other hand, the resin to be obtained finally will be lowered in various performance. In such a case that the residual catalyst would induce a serious reduction in performance, however, the reaction mixture maybe washed with purified water to remove the residual catalyst.

Organic solvents usable in the reaction between the epoxy-modified polysiloxane compound and carbon dioxide include, for example, dimethylformamide, dimethyl sulfoxide, dimethylacetamide, N-methylpyrrolidone, N-ethylpyrrolidone, tetrahydrofuran, and the like. These organic solvents may also be used as mixed systems with other poor solvents, for example, methyl ethyl ketone, xylene, toluene, tetrahydrofuran, diethyl ether, cylohexanone, and the like.

A polysiloxane-modified polyhydroxy polyurethane can be obtained by reacting the 5-membered cyclic carbonate polysiloxane compound of the present invention, which has been obtained as described above, with a polyamine as shown As the polyamine for use in the above-described reaction, a diamine is preferred. No particular limitation is imposed on the diamine, and diamines which have conventionally been used in the production of polyurethane resins are all usable. Illustrative are aliphatic diamines such as methylenediamine, ethylenediamine, trimethylenediamine, 1,3-diaminopropane, hexamethylenediamine and octamethylenediamine; aromatic diamines such as phenylenediamine, 3,3'-dichloro-4,4'-diaminodiphenylmethane, 4,4'-methylenebis(phenylamine), 4,4'-diaminodiphenyl ether, 4,4'-diaminodiphenylsulfone, meta-xylylenediamine and para-xylylenediamine; alicyclic diamines such as 1,4-cyclohexanediamine, 4,4'-diaminocyclohexylmethane, 1,4'-diaminomethylcyclohexane and isophorone diamine; alkanoldiamines such as monoethanoldiamine, ethylaminoethanolamine and hydroxyethylaminopropylamine; and the like. Other diamines are also available on the market these days. These diamine compounds readily available on the market can all be used in the present invention.

The 5-membered cyclic carbonate polysiloxane compound according to the present invention can also be applied as an additive to epoxy resins useful, for example, as paints and sealants, in addition to its use as a raw material for the production of the above-described polysiloxane-modified polyhydroxy polyurethane. Owing to the formation of urethane bonds upon curing of the 5-membered cyclic carbonate polysiloxane compound and the polyamine, it is possible to lessen the occurrence of cracks due to volume shrinkage, said occurrence being a defect of the epoxy resins.

In a coating formed from a resin that has been obtained using as a starting raw material the 5-membered cyclic carbonate polysiloxane compound according to the present invention, the polysiloxane segments in the resin orient in a surface of the coating so that the coating is provided with heat resistance, lubricity and non-tackiness all of which are characteristics of polysiloxane segments. Further, the 5-membered cyclic carbonate polysiloxane compound according to the present invention can also provide, owing to the incorporation of carbon dioxide from the viewpoint of a reduction in greenhouse gas, high-molecular products responsive to the protection of the environment to such extent that cannot be realized with conventional products.

As has been described above, the 5-membered cyclic carbonate polysiloxane compound according to the present invention can be used as a raw material for a polysiloxane-modified polyhydroxy polyurethane resin. The resulting polysiloxane-modified polyhydroxy polyurethane resin is very useful as a raw material for various molding materials, synthetic leather and artificial leather materials, fiber coating materials, surface treatment materials, thermal recording media, strippable materials, paints, and a binder for printing inks; and, when added in epoxy resins, as a raw material for various paints, adhesives, composite materials and sealants.

EXAMPLES

The present invention will next be described in further detail based on specific production examples, examples and comparative examples, although the present invention shall not be limited to these examples. It is to be noted that the terms "parts" and "%" in the following examples are on a mass basis unless otherwise specifically indicated.

Example 1

Production of 5-Membered Cyclic Carbonate Polysiloxane Compound

To a reaction vessel equipped with a stirrer, thermometer, gas inlet tube and reflux condenser, a divalent epoxy-modified polysiloxane represented the below-described formula (A) ("X-22-163", product of Shin-Etsu Chemical Co., Ltd.; epoxy equivalent: 198 g/mol [FIG. 1]; 100 parts), N-methylpyrrolidone (100 parts) and sodium iodide (1.2 parts) were added, followed by stirring into a homogeneous solution. Subsequently, the solution was stirred under heating at 80° C. for 30 hours while bubbling carbon dioxide at a rate of 0.5 L/min.

After completion of the reaction, n-hexane (100 parts) was added to the resultant reaction mixture to dilute it. The diluted reaction mixture was then washed in a separatory funnel three times with purified water (80 parts each time) to eliminate N-methylpyrrolidone and sodium iodide. The resulting n-hexane solution was dried with magnesium sulfate, and was then concentrated to obtain, as a colorless clear liquid, a 5-membered cyclic carbonate polysiloxane compound (1-A) (92 parts, yield: 89.7%).

Figure 2:
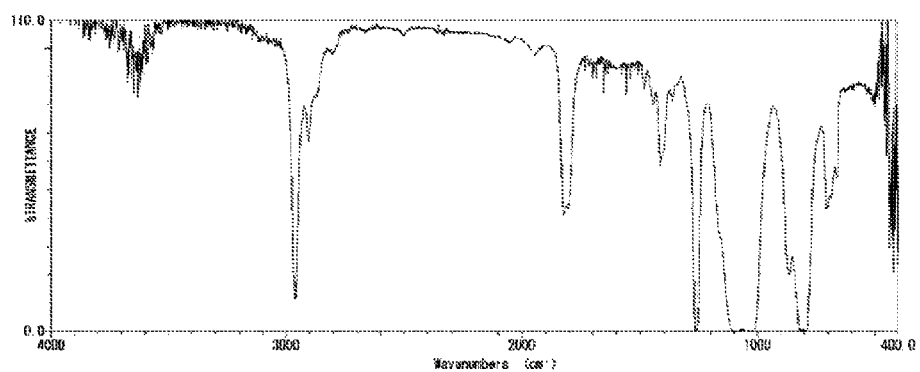
FIG. 2 is an infrared absorption spectrum of a 5-membered cyclic carbonate polysiloxane.

In an infrared absorption spectrum ("FT-720", manufactured by Horiba, Ltd.) of the thus-obtained reaction product, there was observed around 1,800 cm$^{-1}$ an absorption which is attributable to the carbonyl groups in the cyclic carbonate groups and is not found on the raw material [FIG. 2]. The number average molecular weight of the reaction product was 2,450 (polystyrene equivalent; "GPC-8220", manufactured by Tosoh Corporation) [FIG. 3]. In the thus-obtained 5-membered cyclic carbonate polysiloxane compound (1-A), carbon dioxide was fixed as much as 18.1%.

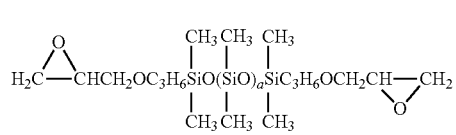

(A)

(a: Value to give a molecular weight of 396)

Example 2

Production of 5-Membered Cyclic Carbonate Polysiloxane Compound

By conducting a reaction as in Example 1 except that a divalent epoxy-modified polysiloxane represented by the below-described formula (B) ("KF-105", product of Shin-Etsu Chemical Co., Ltd.; epoxy equivalent: 485 g/mol) was used in place of the divalent epoxy-modified polysiloxane (A), a 5-membered cyclic carbonate polysiloxane compound (1-B) (99 parts, yield: 91%) was obtained as a colorless clear liquid.

The reaction product was identified by infrared absorption spectroscopy, GPC and NMR. In the thus-obtained 5-membered cyclic carbonate polysiloxane compound (1-B), carbon dioxide was fixed as much as 8.3%.

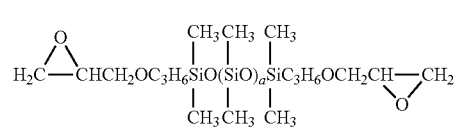

(B)

(a: Value to give a molecular weight of 970)

Example 3

Production of 5-Membered Cyclic Carbonate Polysiloxane Compound

By conducting a reaction as in Example 1 except that a divalent epoxy-modified polysiloxane represented by the below-described formula (C) ("X-22-169AS", product of Shin-Etsu Chemical Co., Ltd.; epoxy equivalent: 533 g/mol) was used in place of the divalent epoxy-modified polysiloxane (A), a 5-membered cyclic carbonate polysiloxane compound (1-C) (71 parts, yield: 68%) was obtained as a colorless clear liquid. The reaction product was identified by infrared absorption spectroscopy, GPC and NMR. In the thus-obtained 5-membered cyclic carbonate polysiloxane compound (1-C), carbon dioxide was fixed as much as 7.6%.

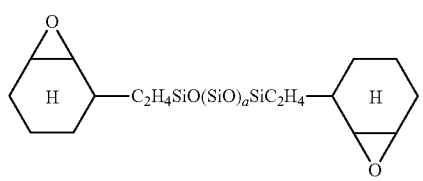

(C)

(a: Value to give a molecular weight of 1,066)

Comparative Example 1

Production of 5-Membered Cyclic Carbonate Compound

By conducting a reaction as in Example 1 except that a divalent epoxy compound represented by the below-described formula (D) ("EPICOAT 828", product of Japan Epoxy Resin Co., Ltd.; epoxy equivalent: 187 g/mol) was used in place of the divalent epoxy-modified polysiloxane (A), a 5-membered cyclic carbonate compound (1-D) (118 parts, yield: 95%) was obtained as a white powder. The reaction product was identified by infrared absorption spectroscopy, GPC and NMR. In the thus-obtained 5-membered cyclic carbonate compound (1-D), carbon dioxide was fixed as much as 19%.

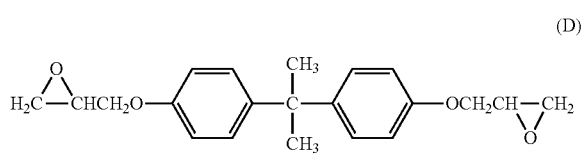

(D)

Polymerization Examples 1 to 3

Production of Polysiloxane-Modified Polyhydroxy Polyurethane Resins

Reaction vessels which were each equipped with a stirrer, thermometer, gas inlet tube and reflux condenser were purged with nitrogen. To the reaction vessels, the 5-membered cyclic carbonate polysiloxane compounds obtained in Examples 1 to 3 were added respectively. To each reaction vessel, N-methylpyrrolidone was added further to adjust a solid content to 35%, followed by stirring into a homogeneous solution. The corresponding amine compound described in Table 1 was then added in the predetermined amount. The resulting mixture was stirred at a temperature of 90° C. for 10 hours so that a reaction was conducted until the amine compound was no longer detected. The three kinds of polysiloxane-modified polyhydroxy polyurethane resins obtained as described above had properties as shown in Table 1.

Comparative Polymerization Example 1

Production of Polyhydroxy Polyurethane Resin

A reaction vessel equipped with a stirrer, thermometer, gas inlet tube and reflux condenser was purged with nitrogen. To the reaction vessel, the 5-membered cyclic carbonate compound obtained in Comparative Example 1 was added. To the reaction vessel, N-methylpyrrolidone was added further to adjust a solid content to 35%, followed by stirring into a homogeneous solution. Hexamethylenediamine was then added in a predetermined amount. The resulting mixture was stirred at a temperature of 90° C. for 10 hours so that a reaction was conducted until the amine compound was no longer detected. The resultant polyhydroxy polyurethane resin had properties as shown in Table 1.

INDUSTRIAL APPLICABILITY

A resin obtainable, as an application example of the present invention, from the novel 5-membered cyclic carbonate polysiloxane compound is excellent in lubricity, abrasion resistance, chemical resistance, non-tackiness, antistatic properties and heat resistance. The use of this resin can, therefore, be expected to provide a variety of products, such as film and molding materials, sealants, various coating materials and various binders, which are excellent in carbon dioxide reduction effect and are useful from the viewpoint of protection of the global environment.

The invention claimed is:

1. A 5-membered cyclic carbonate polysiloxane compound represented by following formula (1):

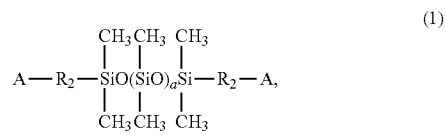

wherein A is

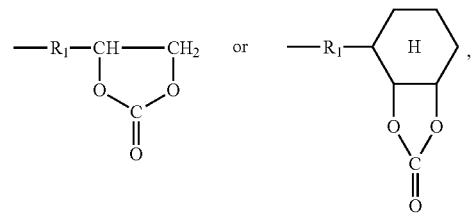

in which $R_1$ is an alkylene group that has from 1 to 12 carbon atoms and may be linked to $R_2$ via —$(C_2H_4O)_b$— or one element selected from the group consisting of O, S, N, a combination of O and —$(C_2H_4O)_b$—, a combination of S and —$(C_2H_4O)_b$—, and a combination of N and —$(C_2H_4O)_b$—, $R_2$ is a direct bond or an alkylene group having from 2 to 20 carbon atoms, $R_2$ may be linked to an alicyclic group or aromatic group, wherein when $R_2$ is the direct bond, a

TABLE 1

|  | Polymerization Example 1 | Polymerization Example 2 | Polymerization Example 3 | Comp. Polymerization Example 1 |
|---|---|---|---|---|
| Carbonate compound (i) | 1-A | 1-B | 1-C | 1-D |
| Amine compound (ii) | HMDA[1] | BAPP[2] | XDA[3] | HMDA[1] |
| Molar ratio (i/ii) | 1.0 | 1.0 | 1.0 | 1.0 |
| Solution viscosity (35% conc., MPa · s) | 1.5 | 1.8 | 1.1 | 1.3 |
| Number average molecular weight | 38,000 | 43,000 | 31,000 | 35,000 |
| Hydroxyl number (mgKOH/g) | 175 | 83 | 76 | 215 |
| Polysiloxane content (%) | 32 | 57 | 62 | 0 |
| Breaking strength (20° C., MPa) | 32.1 | 23.8 | 35.2 | 21.1 |
| Breaking extension (20° C., %) | 15 | 83 | 50 | 15 |
| Surface resistance (20° C. × 46% RH, Ω) | $5.6 \times 10^{12}$ | $2.8 \times 10^{13}$ | $8.2 \times 10^{13}$ | $7.6 \times 10^{10}$ |
| Fixed amount of carbon dioxide (%)[4] | 14.5 | 6.9 | 6.8 | 15.2 |

[1] Hexamethylenediamine
[2] Bis-aminopropylpiperazine
[3] Xylylenediamine
[4] Calculated value carbon in the alkylene group of $R_1$ or a carbon in the —$(C_2H_4O)_b$— group is bonded directly to Si in the formula (1) bound to $R_2$, b stands for a number of from 1 to 300, and a stands for a number of from 1 to 300.

2. A process for producing the 5-membered cyclic carbonate polysiloxane compound according to claim 1, which comprises reacting an epoxy-modified polysiloxane compound represented by following formula (2) with carbon dioxide:

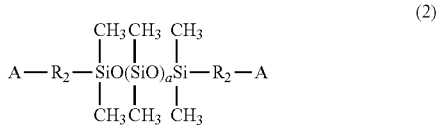
(2)

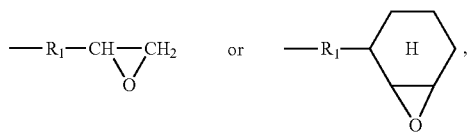

in which $R_1$ is an alkylene group that has from 1 to 12 carbon atoms and may be linked to $R_2$ via —$(C_2H_4O)_b$— or one element selected from the group consisting of O, S, N, a combination of O and —$(C_2H_4O)_b$—, a combination of S and —$(C_2H_4O)_b$—, and a combination of N and —$(C_2H_4O)_b$—, $R_2$ is a direct bond or an alkylene group having from 2 to 20 carbon atoms, $R_2$ may be linked to an alicyclic group or aromatic group, wherein when $R_2$ is the direct bond, a carbon in the alkylene group of $R_1$ or a carbon in the —$(C_2H_4O)_b$— group is bonded directly to Si in the formula (2) bound to $R_2$, b stands for a number of from 1 to 300, and a stands for a number of from 1 to 300.

3. The 5-membered cyclic carbonate polysiloxane compound according to claim 1, wherein $R_1$ may be linked to $R_2$ via at least one group selected from the group consisting of —$(C_2H_4O)_b$— and O, $R_2$ is not linked to an alicyclic group or aromatic group, and a in the formula (1) stands for a number from 1 to 9.2.

4. The 5-membered cyclic carbonate polysiloxane compound according to claim 1, wherein $R_1$ may be linked to $R_2$ via at least one group selected from the group consisting of —$(C_2H_4O)_b$— and O, $R_2$ is not linked to an alicyclic group or aromatic group, and a in the formula (1) stands for a number from 8.2 to 9.2.

5. The process according to claim 2, wherein $R_1$ may be linked to $R_2$ via at least one group selected from the group consisting of —$(C_2H_4O)_b$— and O, $R_2$ is not linked to an alicyclic group or aromatic group, and a in the formula (1) stands for a number from 1 to 9.2.

6. The process according to claim 2, wherein $R_1$ may be linked to $R_2$ via at least one group selected from the group consisting of —$(C_2H_4O)_b$— and O, $R_2$ is not linked to an alicyclic group or aromatic group, and a in the formula (1) stands for a number from 8.2 to 9.2.

7. The 5-membered cyclic carbonate polysiloxane compound according to claim 1, wherein $R_1$ may be linked to $R_2$ via at least one group selected from the group consisting of O, S, N, —$(C_2H_4O)_b$—, and the combination of O and —$C_2H_4O)_b$—.

8. The process for producing the 5-membered cyclic carbonate polysiloxane compound according to claim 2, wherein $R_1$ may be linked to $R_2$ via at least one group selected from the group consisting of O, S, N, —$(C_2H_4O)_b$—, and the combination of O and —$C_2H_4O)_b$—.

* * * * *